(12) United States Patent
Tan et al.

(10) Patent No.: US 7,319,151 B1
(45) Date of Patent: Jan. 15, 2008

(54) THERMALLY CROSS-LINKABLE TWO-PHOTON CHROMOPHORES

(75) Inventors: Loon-Seng Tan, Centerville, OH (US); Ramamurthi Kannan, Cincinnati, OH (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 47 days.

(21) Appl. No.: 11/357,467

(22) Filed: Feb. 13, 2006

Related U.S. Application Data

(60) Provisional application No. 60/656,508, filed on Feb. 25, 2005.

(51) Int. Cl.
   *C07D 277/60* (2006.01)
(52) U.S. Cl. ..................................... 548/152
(58) Field of Classification Search ................ 548/152
   See application file for complete search history.

(56) References Cited

U.S. PATENT DOCUMENTS

| | | |
|---|---|---|
| 6,300,502 B1 | 10/2001 | Kannan et al. |
| 6,555,682 B1 | 4/2003 | Kannan et al. |
| 6,730,793 B1 | 5/2004 | Kannan et al. |
| 6,867,304 B1 | 3/2005 | Tan et al. |

OTHER PUBLICATIONS

Belfield et al., "Synthesis of New Two-Photon Absorbing Fluorene Derivatives via Cu-Mediated Ullmann Condensation" Journal of Organic Chemistry, vol. 65, No. 15, 2000.*

Tan, Loon-Seng; Kannan, Ramamurthi; Dombroskie, Ann G.; Simko, Sharon R.; Houtz, Marlene D.; He, Guang S.; Lin, Tzu-Chau; Prasad, Paras N. "Synthesis and characterization of thermally cross-linkable, two-photon responsive chromophores." Polymer Preprints (American Chemical Society, Division of Polymer Chemistry) (Mar. 2004), 45(1), 901-902.

* cited by examiner

*Primary Examiner*—Kamal A. Saeed
(74) *Attorney, Agent, or Firm*—AFMCLO/JAZ; Bart S. Hersko

(57) ABSTRACT

Provided are new two-photon absorbing chromophores of the formula:

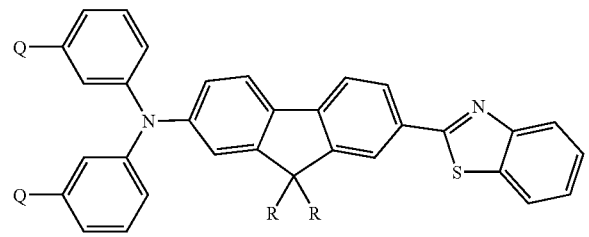

wherein R is an alkyl group having 1 to 20 carbon atoms and Q is OH, OMe, propargyloxy-(O—$CH_2$—C≡CH), methyl-propargyloxy-(O—$CH_2$—C≡C—$CH_3$), allyloxy-(O—$CH_2$—C=$CH_2$), 1-methyl-allyloxy(O—$CH_2$—CH=$CHCH_3$) and 3-methyl-allyloxy (O—CH($CH_3$)—CH=$CH_2$).

7 Claims, No Drawings

THERMALLY CROSS-LINKABLE TWO-PHOTON CHROMOPHORES

CROSS REFERENCE TO RELATED APPLICATION

This application claims priority of the filing date of Provisional Application Ser. No. 60/656,508, filed Feb. 25, 2005.

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with large effective two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (TPA), two quanta of photons may be absorbed from a single light source (degenerate TPA) or two sources of different wavelengths (non-degenerate TPA). Although multiphoton absorption processes have been known since 1931, this field remained dormant largely due to the lack of TPA-active materials with sufficiently large cross-sections. In the mid-1 990s, several new classes of chromophores exhibiting very large effective TPA cross-section ($\sigma_2'$) values were reported. In conjunction with the increased availability of ultrafast high-intensity lasers, the renewed interest has not only sparked a flurry of activities in the preparation of novel dye molecules with enhanced $\sigma_2'$ values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-V is upconversion; (b) deeper penetration of incident light; (c) highly localized excitation allowing precision control of in-situ photochemical events in the absorbing medium, thereby minimizing undesirable activities such as photodegradation or photobleaching; (d) fluorescence when properly manipulated allows information feedback. It is anticipated that further ingenious utilization of these basic characteristics will lead to practical applications other than those already emerged in such diverse areas as fluorescence imaging, data storage, eye and sensor protection, microfabrication of microelectromechanical systems (MEMS), photodynamic therapy, etc.

Accordingly, it is an object of the present invention to provide new TPA chromophores with the capability to undergo thermally-induced polymerization or cross-linking reactions. This capability is provided by having two or more unsaturated hydrocarbon moieties such as allyl or propargyl groups strategically positioned in the chromophoric structures. Upon activation by heat, UV or electron beam, such unsaturated moieties are known to engage in free-radical reactions and polymerization by themselves or with appropriate substrates or host materials.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided new TPA chromophores of the formula:

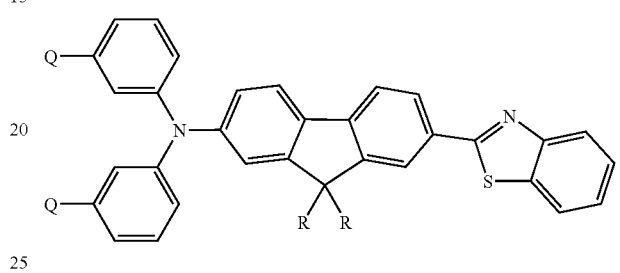

wherein R is an alkyl group having 1 to 20 carbon atoms and Q is OH, O—$CH_3$, propargyloxy-(O—$CH_2$—C—CH), methylpropargyloxy- (O—$CH_2$—C—C—$CH_3$), allyloxy- (O—$CH_2$—C=$CH_2$), 1-methyl-allyloxy (O—$CH_2$—CH=CH—$CH_3$) and 3-methyl-allyloxy (O—CH($CH_3$)—CH=CH?). Preferably, R is ethyl and Q is OH, O—$CH_3$, O—$CH_2$—C—CH, O—$CH_2$—C=$CH_2$ or a isomeric mixture of O—$CH_2$—CH—CH—$CH_3$.(85-mol %) and O—CH($CH_3$)—CH=$CH_2$ (15 mol %).

The chromophores of this invention can be synthesized following the procedures given in the following examples which illustrate the invention:

EXAMPLE 1

2,7-Dibromofluorene

To a mechanically stirred mixture of fluorene (113.76 g., 0.68 mol.), iodine (1.96 g., 0.0077 mol.), and methylene chloride (750 ml), bromine (74 ml, 1.44 mol.) diluted with methylene chloride (100 ml) was added dropwise at room temperature over a period of 1.5 hours. After 5 minutes, a solution of sodium bisulfite (15.0 g.) in water (100 ml) was added and the mixture was stirred for 30 minutes, when the mixture became colorless. Water (750 ml) was then added, and methylene chloride was distilled off. The product slurry was filtered and the product was air-dried, 220.5 g., m.p. 156-160° C. This material was used in the next step without further purification.

EXAMPLE 2

9,9-Diethyl-2,7-dibromofluorene

To a mechanically stirred mixture of 2,7-dibromofluorene (66.5 g., 0.205 mol.), powdered potassium hydroxide (56.0 g., 1.0 mol.), potassium iodide (3.4 g.) and DMSO (150 ml), cooled to 10° C., ethyl bromide (40 ml, 58.4 g. 0.536 mol.)

was added dropwise over 45 minutes. The mixture turned from red to light purple. After allowing the temperature to warm to 20° C., the mixture was left overnight to stir and poured into water, 77.0 g (98.7% yield), m.p. 144-153° C. The product was then recrystallized from hexane (550 ml) With charcoal treatment, and collected in two crops, m.p. 154-157° C. and 153-154° C., totaling 60.36 g. (77.4% yield).

EXAMPLE 3

9,9-Diethyl-7-bromo-fluorene-2-carboxaldehyde

To a mechanically stirred solution of 9,9-diethyl-2,7-dibromofluorene (59.38 g., 0.1563 mol.), in THF (325 ml), cooled in dry ice-ethanol bath, n-butyl lithium (104 ml of 1.6M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 of concentrated hydrochloric acid diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane-ethyl acetate (9:1), to get colorless solids, 40.29 g. (78.4% yield) m.p. 126-128° C. The mother liquor after chromatography over 150 g. silica gel, elution with 1:1 heptane-toluene, and trituration of residual solids in hexanes gave additional product, 6.56 g. (12.8% yield, total 91% yield), m.p. 126-128° C. Mass Spectrum (m/z): 328, 330, (M$^+$). A sample for analysis was prepared by recrystallization from hexanes, m.p. 127-129° C. Anal. Calcd. for $C_{18}H_{17}BrO$: C, 65.55; H, 5.20; Br, 24.27%. Found: C, 65.60; H, 5.51; Br, 24.71%.

EXAMPLE 4

2-(7-Bromo-9,9-diethylfluoren-2-yl)benzothiazole

A mixture of 9,9-diethyl-7-bromo-fluorene-2-carboxaldehyde (49.35 g., 0.15 mol.), 2-aminothiophenol (20 ml. 0.187 mol., 1.25 eq.), and DMSO (110 nl) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the product benzothiazole, 45.69 g., m.p. 133.6-135° C. An additional 6.6 g., m.p. 134.6-135.5° C., was obtained by chromatography of the ethanol filtrate. Total recovery was 52.29 g. (80.3% yield). Mass Spec: m/z 433, 435, (M$^+$). Anal. Calcd for $C_{24}H_{20}BrNS$: C, 66.37; H, 4.64; Br, 18.40; N, 3.23; S 7.37%. Found: C, 66.46; H, 4.52; Br, 18.54; N, 3.14; S, 7.19%.

EXAMPLE 5

7-Benzothiazol-2-yl-9,9-diethylfluoren-2-yl)bis(3-methoxyphenyl)amine (AF-366)

A mixture of 7-benzothiazol-2-yl-9,9-diethyl-2-bromofluorene (10.85 g, 25 mmol), 3,3'-dimethoxydiphenylamine (6.87 g, 30 mmol) and toluene (100 ml) was azeotroped dry under nitrogen and cooled. Bis(dibenzylideneacetone)palladium (0) (0.28 g, 0.49 mmol), bis(diphenylphosphino)ferrocene (0.25 g, 0.45 mmol) and sodium-t-butoxide (3.5 g, 36.4 mmol) were then added and the mixture was heated to 100° C. After 24 hours, the mixture was cooled, diluted with toluene and filtered. The filtrate was washed with water, dried and concentrated. The residue was chromatographed over silica gel. Elution with toluene-heptane (3:1) gave the product, which was recrystallized from a mixture of toluene-heptane, m.p. 178-179.5° C., 11.13 g (76% yield). $^1$H NMR (CDCl$_3$) δ ppm: 0.35-0.41 (t, 6H), 1.91-2.14 (m, 4H), 3.69 (s, 6H), 6.54-6.74, 7.05-7.68, 7.84-8.10 (m, 18H). $^{13}$C NMR: 8.61, 32.66, 55.18, 56.44 (sp$^3$C), 108.62, 109.77, 116.66, 119.16, 119.42, 121.00, 121.44, 121.52, 122.94, 123.77, 124.95, 126.28, 127.28, 129.82, 131.55, 134.91, 135.61, 144.48, 147.84, 148.94, 150.67, 151.99, 154.24, 160.46, 168.81 (Sp$^2$C). Anal. Calcd for C, 78.33; H, 5.88; N, 4.81; S, 5.49%. Found: C, 78.26; H, 5.96; N, 4.68; S 5.47%.

EXAMPLE 6

(7-Benzothiazol-2-yl-9,9-diethylfluorene-2-yl)bis(3-hydroxyphenyl)amine

A mixture of 7-benzothiazol-2-yl-9,9-diethylfluorene-2-yl)bis(3-methoxyphenyl)amine (example 6; 1 g), and pyridine hydrochloride (10 g) was held at 200° C. in an oil bath for 10 hours, cooled, slurried in water, and the red solids were collected. These were slurried in dilute ammonium hydroxide to get the greenish yellow solid product, 1.13 g, m.p. 314-316° C. Mass Spectrum (m/z): 554 (M$^+$). Anal. Calcd for $C_{36}H_{30}N_2O_2S$: C, 77.95; H, 5.45; N, 5.05; S, 5.78%. Found: C, 77.74; H, 5.39; N, 4.83; S, 5.78%.

EXAMPLE 7

7-(Benzothiazol-2-yl-9,9-diethyl)-fluoren-2-yl)-bis(3-prop-2-ynyloxyphenyl)-amine, (AF-346)

A mixture of (7-benzothiazol-2-yl-9,9-diethylfluorene-2-yl)bis(3-hydroxyphenyl)amine (example 6; 3.67 g, 6.6 mmol), propargyl bromide (80% solution, 7 ml, 47 mmol), potassium carbonate (2.76 g, 20 mmol) and DMF (45 ml) was stirred at room temperature for 20 hr, poured into water and extracted into toluene. The toluene extract was washed with water, dried and concentrated. The residue was chromatographed over silica gel. The product, 1.82 g (44% yield), was obtained from 3:1 toluene-heptane eluent followed by recrystallization from toluene-heptane, m.p. 154.1-155.9° C. Mass spec: m/z 630 (M$^+$), IR (cm$^1$): 3291, 2100. $^1$H. NMR (CDCl$_3$) δ ppm: 0.33-0.40.(t, 6H), 1.91-2.14 (m, 4H), 2.48-2.50 (t, 2H), 4.57-4.60 (dd, 4H), 6.63-6.77 (m, 6H), 7.07-7.1 (m, 8H), 7.88-8.09 (m, 4H). $^{13}$C NMR: 8.61, 32.63, 55.78, 56.44 (sp$^3$C), 75.59, 78.41 (sp C), 109.14, 110.78, 117.29, 119.48, 119.57, 121.06, 121.44, 121.52, 122.94, 124.14, 124.98, 126.28, 127.28, 129.85, 131.63, 134.91, 135.92, 144.36, 147.56, 148.82, 150.72, 152.08, 154.21, 158.41, 168.78 (sp$^2$C). Anal. Calcd for $C_{42}H_{34}N_2O_2S$: C, 79.97; H, 5.43; N, 4.44; S, 5.08%. Found: C, 79.87; H, 5.64; N, 4.31; S, 4.80%.

EXAMPLE 8

(7-Benzothiazol-2-yl-9,9-diethyl)fluoren-2-yl-bis(3-but-2-ynyloxyphenyl)-amine, (AF-346-1)

A mixture of (7-benzothiazol-2-yl-9,9-diethylfluorene-2-yl)bis(3-hydroxyphenyl)amine (example 6, 2.77 g, 5 mmol), 1-bromo-2-butyne (1.5 ml, 17 mmol), potassium carbonate (2.08 g, 15 mmol) and DMF (34 ml) was stirred at room temperature for 3 days, poured into water, and extracted into toluene. The toluene extract was washed with water, dried and concentrated. The residue was chromatographed over silica gel to obtain the product, 2.1 g (67% yield), m.p. 150.0-151.9° C. Mass spec: m/z 658 (M$^+$). IR: 2245 cm$^{-1}$. $^1$H NMR (CDCl$_3$) δ ppm: 0.35-0.41 (t, 6H), 1.81-1.83 (t, 6H), 1.91-2.11 (m, 4H), 4.54, 4.55 (br s, 4H), 6.62-6.76 (m, 6H), 7.05-7.24 (m, 4H), 7.33-7.51 (m, 2H), 7.59-7.70 (m, 2H), 7.87-8.09 (m, 4H). $^{13}$C NMR: 3.69, 8.55, 8.61, 32.63, 56.39 (sp$^3$C), 73.81, 73.86, 83.66, 83.71 (spC), 109.11, 110.75, 117.00, 119.36, 120.95, 121.47, 122.91, 123.94, 124.92, 126.22, 127.25, 129.70, 131.52, 134.86, 134.91, 135.66, 135.72, 144.36, 144.42, 147.67, 147.73, 148.77, 148.82, 150.67, 150.72, 151.96, 152.02, 154.18, 154.24, 158.70, 158.76, 168.78 (sp$^2$C). Anal. Calcd for C$_{44}$H$_{38}$N$_2$O$_2$S: C, 80.21; H, 5.81; N, 4.25; S, 4.86%. Found: C, 79.99; H, 6.05; N, 4.03; S, 4.89%.

EXAMPLE 9

(7-Benzothiazol-2-yl-9,9-diethyl)fluoren-2-yl-bis(3-prop-2-enyloxyphenyl)amine, (AF-347)

To a round-bottomed flask that was cooled by an ice bath to 10° C. the following was added: (7-benzothiazol-2-yl-9,9-diethylfluorene-2-yl)bis(3-hydroxyphenyl)amine (example 6; 3.49 g, 0.0063 mmol), allyl bromoide (1.63 ml, 0.0189 mmol), potassium carbonate (2.63 g, 0.019 mmol), and DMF (43 mL). This was allowed to stir for 3.5 days at room temperature and monitored with thin layer chromatography until reaction completion, and the flask contents were poured into water. Toluene was used to extract the crude product, which was washed several times with water, dried over magnesium sulfate, filtered and concentrated. A brown oil resulted. Further purification involved passing the oil through a silica gel column and eluting with a 3/1 (v/v) toluene-heptane mixture. The product was collected in several fractions, which were concentrated. Isopropanol was added and the fractions were allowed to stand for several days in the refrigerator until a bright yellow/green solid formed, 1.59 g (37% yield), m.p. 110-114° C. Mass spec: m/z, 634 (M$^+$). $^1$H NMR (CDCl$_3$) δ ppm: 0.35-0.41 (t, 6H), 1.94-2.14 (m, 4H), 4.41-4.43 (dd, 4H), 5.21-5.37 (m, 4H), 5.92-6.04 (m, 2H), 6.59-6.73 (m, 6H), 7.05-7.70 (m, 8H), 7.86-8.09 (m, 4H). $^{13}$C NMR: 8.61, 32.63, 56.41, 68.71 (sp$^3$C), 109.29, 110.61, 116.80, 117.69, 119.16, 119.39, 121.01, 121.38, 121.52, 122.91, 123.74, 124.95, 126.25, 127.28, 129.79, 131.52, 133.10, 134.89, 135.58, 144.45, 147.79, 148.85, 150.67, 151.96, 154.21, 159.45, 168.78 (sp$^2$C).

EXAMPLE 10

Isomeric mixture (85/15) of (7-benzothiazol-2-yl-9,9-diethyl)fluoren-2-yl-bis(4-crotyloxyphenyl)amine (85%) and (7-benzothiazol-2-yl-9,9-diethyl)fluoren-2-yl-bis[4-(1-methylprop-2-enyloxy)phenyl]amine (15%), (AF-347-1)

A mixture of (7-benzothiazol-2-yl-9,9-diethylfluorene-2-yl)bis(3-hydroxyphenyl)amine (2.77 g, 5 mmol), trans-1-bromo-2-butene (crotyl bromide, tech 85% containing 15% 3-bromo-1-butene, 1.54 ml, 12.7 mmol), potassium carbonate (2.08 g, 15 mmol), and DMF (34 ml) was stirred at room temperature for 4 days, warmed to 45° C. for 4 hours, and poured into water. The mixture was then extracted into toluene; toluene extract washed with water, dried and concentrated. The residue was chromatographed over silica gel. Elution with toluene-heptane (3:1) afforded the product as a foam, in two crops totaling 60% yield; 1.5 g (45%) and m.p. 45-50° C., 0.52 g (15% yield). Mass spec: m/z, 662 (M$^+$). $^1$H NMR (CDCl$_3$) δ ppm: 0.35-0.40 (t, 6H), 1.36, 1.38(d), 1.63, 1.65(d), 1.70, 1.73 (dd, 6H, all 3 isomers), 1.91-2.14 (m, 4H), 4.34, 4.35 (d), 4.48, 4.50 (d, 4H), 5.63-5.83 (m, 4H), 6.57-6.73 (m, 6H), 7.04-7.25 (m, 4H), 7.34-7.52 (m, 2H), 7.59-7.71 (m, 2H), 7.88-8.09 (m, 4H). $^{13}$C NMR: 8.61, 17.85, 32.63, 56.41, 68.62 (sp$^3$C), 109.28, 110.61, 116.69, 119.16, 119.39, 120.98, 121.41, 121.52, 122.91, 123.74, 124.95, 125.90, 126.25, 127.28, 129.76, 130.68, 131.49, 134.91, 135.52, 144.48, 147.87, 148.88, 150.67, 151.96, 154.24, 159.57, 168.84 (sp$^2$C). Anal. Calcd for C$_{44}$H$_{42}$N$_2$O$_2$S: C, 79.70; H, 6.38; N, 4.22; S, 4.83%. Found: C, 79.71; H, 6.71; N, 4.12; S, 4.63%.

The TPA values of the chromophores are shown in the following table. The effective TPA cross-sections ($\sigma_2'$, 1 GM=10$^{-50}$ cm$^4$-sec/photon-molecule; ±15% uncertainty) were measured by a nonlinear transmission (NLT) technique in THF solution (0.02 M) at 800 nm with ~8 ns laser pulses. The TPA and linear optical properties of the parent chromophore AF-240 are included for comparison:

| Chromophore | $\lambda_{max}$ (nm) Linear Abs. (Upcov. Emission.) | β cm/GW at 0.2 mol/L | $\sigma_2' \times 10^{-48} \left(\dfrac{cm^4 \cdot sec}{ph \cdot molecule}\right)$ | $\sigma_2'/MW \times 10^{-50} \left(\dfrac{cm^4 \cdot sec \cdot mole}{ph \cdot molecule \cdot g}\right)$ |
|---|---|---|---|---|
| AF-240* | 392 (479) | 4.7 | 97.5 | 19 |
| AF-336 (OMe) | 392 (470) | 4.4 | 90.1 | 15.5 |
| AF-346 | 390 (470) | 5.1 | 100.4 | 16.5 |
| AF-346-1 | 392 (473) | 4.0 | 83.40 | 12.7 |
| AF-347 | 392 (473) | 3.2 | 65.6 | 10.3 |
| AF-347-1 | 392 (473) | 4.3 | 87.9 | 13.3 |

*(7-benzothiazol-2-yl-9,9-diethylfluoren-2-yl)diphenylamine

The AFX chromophores were subjected to thermal characterization via differential scanning calorimetry (DSC, at 10° C./min, N$_2$) and their thermal properties are shown in the following table. As expected, all except AF-347-1 are crystalline compounds with melting temperatures (T$_m$) ranges from 112° C. to 153° C., and upon rescan after previously heating to 50° C. beyond each T$_m$, both AF-346 and AF-347 displayed glass-transition (T$_g$) behaviors ~39-40° C. Since AF-347-1 is actually a mixture of isomers, it showed only a T$_g$ at 25° C. Their thermally-induced polymerization commenced about 230-245° C. and at the maximum around 261-283° C. In comparing the values for the enthalpy of reaction, it can be concluded that propargyl groups are more reactive than the allyl group and the methyl substitution in both cases significantly curtailed the thermal reactivity. The cross-linked nature of the cured materials under DSC conditions was supported by their insolubility and swelling in the solvents, e.g., toluene, for the monomers.

| AFX | T$_g$ (° C.)* | T$_m$ (° C.)** | T$_{onset}$ (° C.)*** | T$_{max}$ (° C.)**** | ΔH$_{rxn}$ (J/g) |
|---|---|---|---|---|---|
| AF-346 | 39.5 | 152.5 | 229.9 | 268.3 | 553.3 |
| AF-346-1 | — | 150.9 | 244.6 | 283.1 | 423.4 |
| AF-347 | 39.7 | 111.7 | 233.2 | 263.8 | 164.5 |
|  |  | 120.2 |  |  |  |
| AF-347-1 | 24.9 | — | 232.3 | 260.6 | 109.9 |

Glass transition temperatures
*Melting temperatures
**Onset temperature of thermal cure
***Peak temperature of thermal cure
****Heat of reaction (cure)

Having thus described exemplary embodiments of the present invention, it should be noted by those skilled in the art that the disclosures herein are exemplary only and that alternatives, adaptations and modifications may be made within the scope of the present invention.

We claim:
1. A chromophore of the formula:

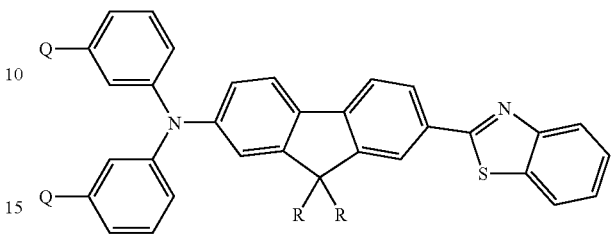

wherein each R is an ethyl group and Q is OH, O—CH$_2$—C≡CH, O—CH$_2$C≡C—CH$_3$, O—CH$_2$CH═CH$_2$, O—CH$_2$—CH═CH—CH$_3$, O—CH(CH$_3$)—CH═CH$_2$, or mixtures thereof.

2. The chromophore of claim 1 wherein Q is OH.
3. The chromophore of claim 1 wherein Q is O—CH$_2$—C≡CH.
4. The chromophore of claim 1 wherein Q is O—CH$_2$—C≡C—CH$_3$.
5. The chromophore of claim 1 wherein Q is O—CH$_2$—CH═CH$_2$.
6. The chromophore of claim 1 wherein Q is O—CH(CH$_3$)—CH═CH$_2$.
7. An isomeric chromophore mixture containing about 85 mol % of the chromophore of claim 4 and about 15% of the chromophore of claim 6.

* * * * *